(12) United States Patent
Torres et al.

(10) Patent No.: US 7,914,735 B2
(45) Date of Patent: Mar. 29, 2011

(54) USE OF PHYSICAL BARRIERS TO MINIMIZE EVAPORATIVE HEAT LOSSES

(75) Inventors: Francisco E. Torres, San Jose, CA (US); Michael Chabinyc, Mountain View, CA (US); Scott Elrod, La Honda, CA (US); Eric Peeters, Fremont, CA (US); Gregory B. Anderson, Emerald Hills, CA (US); Alan G. Bell, Palo Alto, CA (US); Richard H. Bruce, Los Altos, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 1089 days.

(21) Appl. No.: 11/037,666

(22) Filed: Jan. 18, 2005

(65) Prior Publication Data
US 2006/0159585 A1 Jul. 20, 2006

(51) Int. Cl.
*G01N 33/00* (2006.01)
(52) U.S. Cl. ........ 422/51; 422/50; 422/68.1; 422/82.01; 422/82.12; 422/99
(58) Field of Classification Search ............... 422/50, 422/68.1, 82.01, 82.12, 99, 100
See application file for complete search history.

(56) References Cited

U.S. PATENT DOCUMENTS

| | | | |
|---|---|---|---|
| 5,967,659 A | 10/1999 | Plotnikov et al. | |
| 6,037,168 A * | 3/2000 | Brown | 435/288.3 |
| 6,079,873 A | 6/2000 | Cavicchi et al. | |
| 6,096,559 A | 8/2000 | Thundat et al. | |
| 6,193,413 B1 | 2/2001 | Lieberman | |
| 6,380,605 B1 | 4/2002 | Verhaegen | |
| 6,436,346 B1 * | 8/2002 | Doktycz et al. | 422/51 |
| 6,545,334 B2 | 4/2003 | Verhaegen | |
| 2002/0093070 A1 | 7/2002 | Verhaegen | |
| 2003/0152128 A1 | 8/2003 | Verhaegen | |
| 2003/0183525 A1 | 10/2003 | Elrod et al. | |
| 2003/0186453 A1 | 10/2003 | Bell et al. | |
| 2004/0038227 A1 | 2/2004 | Verwaerde et al. | |
| 2004/0038228 A1 | 2/2004 | Verhaegen | |
| 2004/0110301 A1 | 6/2004 | Neilson et al. | |
| 2004/0241869 A1 | 12/2004 | Davies et al. | |

FOREIGN PATENT DOCUMENTS

| | | |
|---|---|---|
| EP | 1 351 052 | 10/2003 |
| WO | WO9954730 | * 10/1999 |

OTHER PUBLICATIONS

European Search Report, Application No. EP 06 10 0370, Search Completed Jun. 16, 2006, Place of Search, The Hague, 6 pages.

* cited by examiner

Primary Examiner — Sam Siefke
(74) Attorney, Agent, or Firm — Fay Sharpe LLP

(57) ABSTRACT

A detection system includes a detection device and an anti-evaporation device. The detection device comprises a region configured to merge at least two small drops and to detect a potential transient signal generated by the merger of the drops. The an anti-evaporation is configured to enclose the region and limit evaporation from the region. A method for detecting a signal includes the following steps: depositing drops of potentially reactive chemical solutions on a detection device within a drop-merging region; placing an anti-evaporation device over the drop-merging region to form a seal around the drop-merging region; merging the drops of potentially reactive chemical solutions; and measuring a signal occurring within the merged solution drops.

19 Claims, 12 Drawing Sheets

FIG. 1
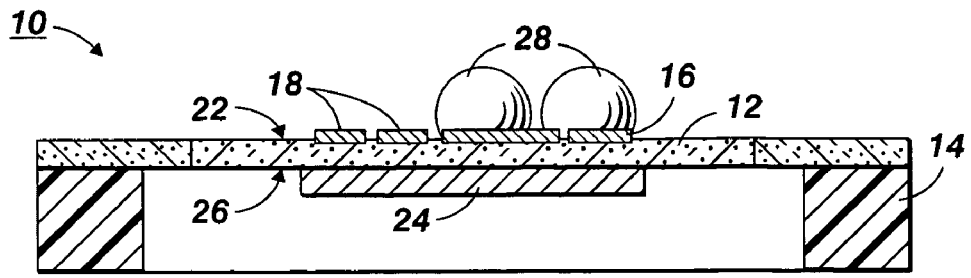
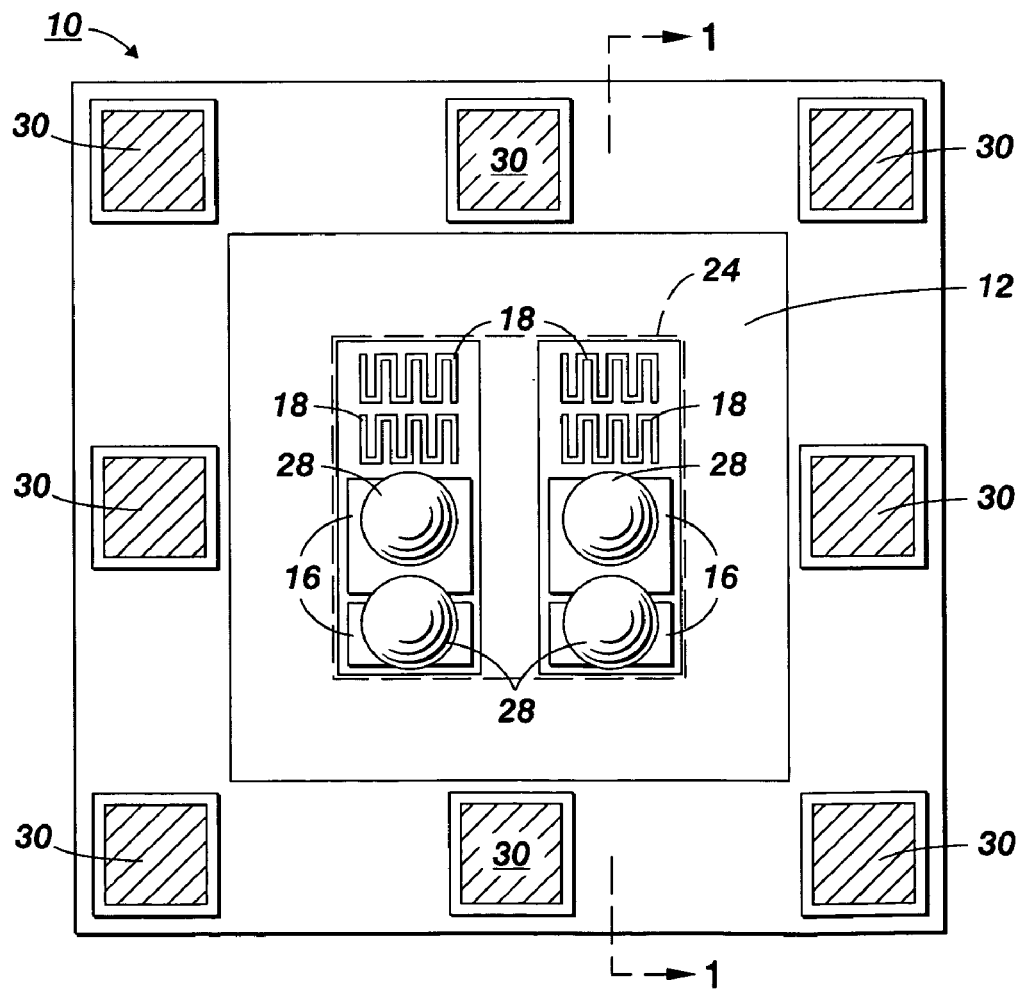
FIG. 2

FIG. 8
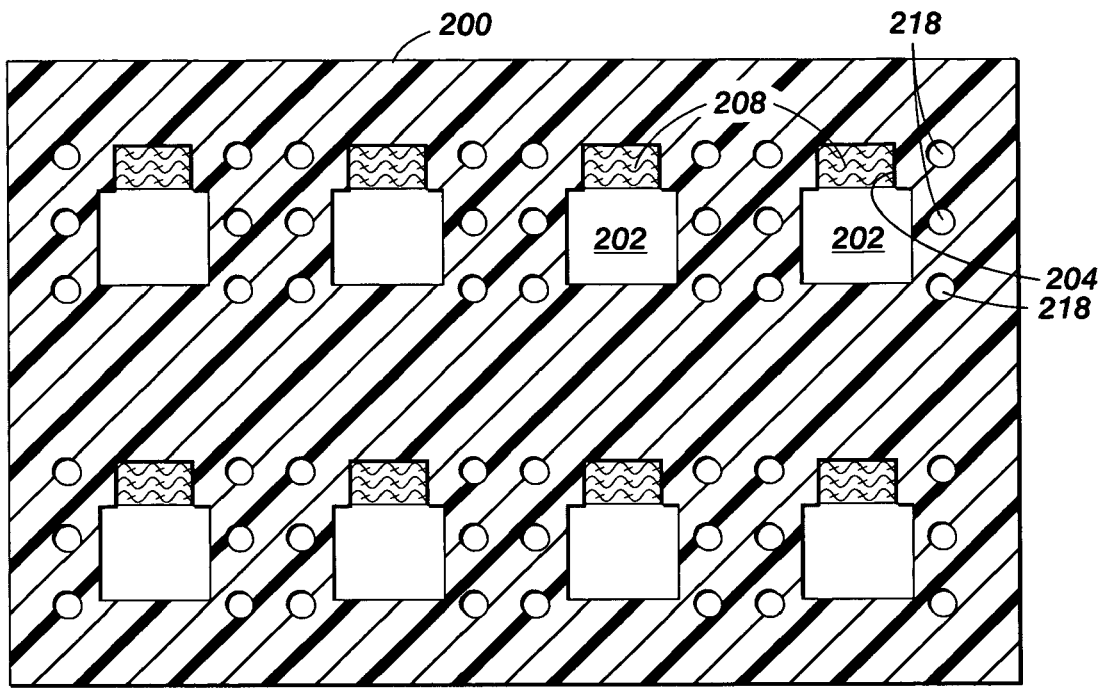
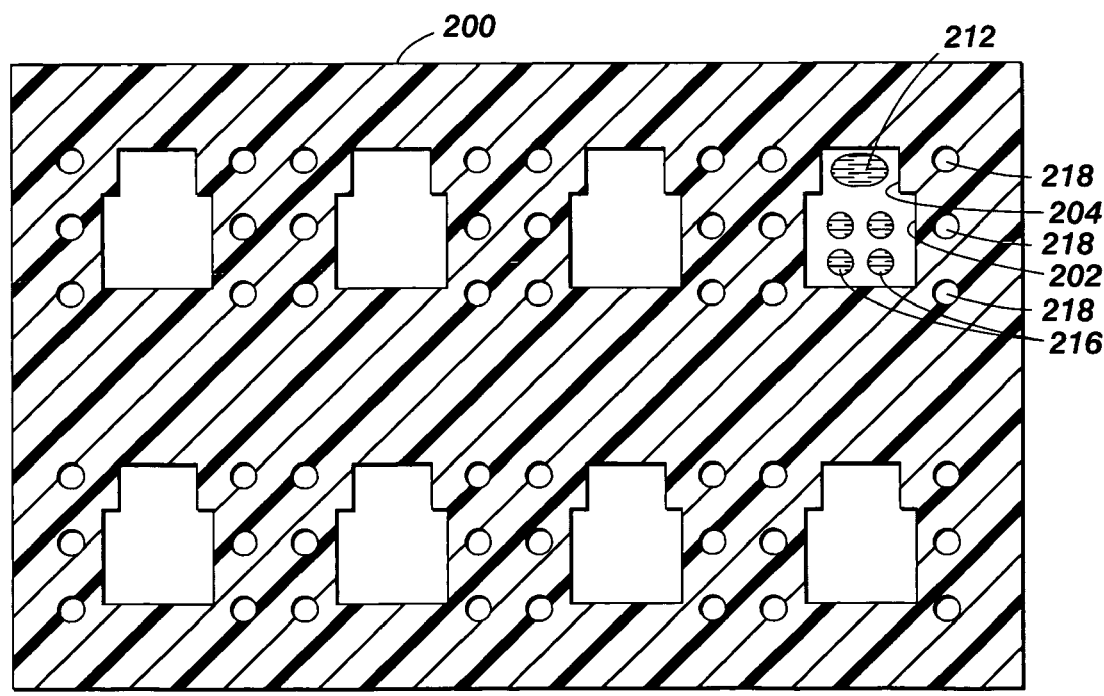
FIG. 9

FIG. 17
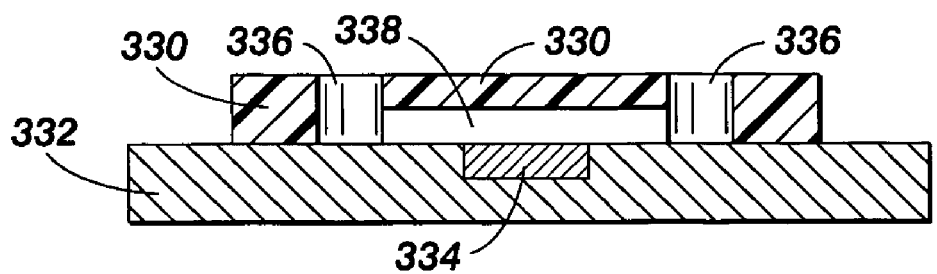
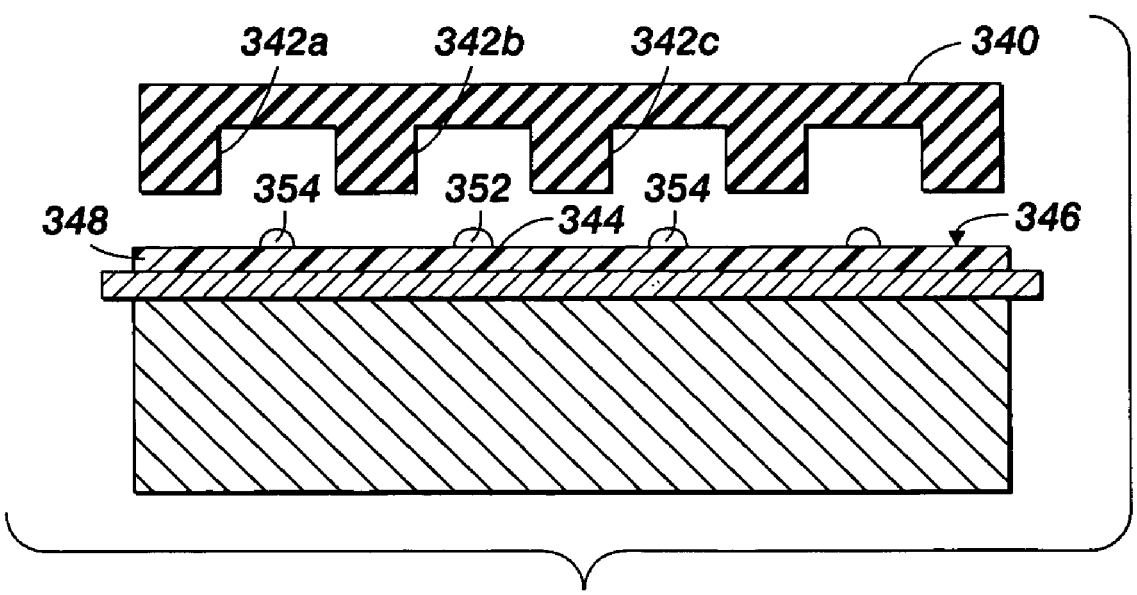
FIG. 18

USE OF PHYSICAL BARRIERS TO MINIMIZE EVAPORATIVE HEAT LOSSES

INCORPORATION BY REFERENCE

U.S. Pat. Nos. 5,967,659; 6,079,873; 6,096,559; 6,193,413; 6,545,334 and 6,380,605 and U.S. Patent Application Pub. Nos. 2003/0186453, 2003/0183525, 2004/0038228, 2004/0038227, 2003/0152128, and US20020093070 are each incorporated in their entirety by reference herein

BACKGROUND

Calorimetry is used to measure enthalpic changes, including enthalpic changes arising from reactions, phase changes, changes in molecular conformation, temperature variations, and other variations of interest that may occur for a particular specimen. By measuring enthalpic changes over a series of conditions, other thermodynamic variables may be deduced. Calorimetry measurements are commonly used in biophysical and biochemical studies to determine energy changes as indications of biochemical reactions in a specimen. There is a great interest in developing ultra-miniature microcalorimeter devices that require very small volumes of sampled media, e.g. small drops, for accurate detection and measuring of biochemical reactions on, or in proximity to, the microcalorimeter and which can be applied in a manner to quickly measure large numbers of reactions.

A known calorimeter device includes drop merging electrodes and thermometers residing on a substrate. A protein drop and a ligand drop can be deposited at different locations on a drop merging device comprising electrodes. A voltage difference is applied between two adjacent electrodes and electrostatic forces cause the drops to move toward one another until they merge. The thermometers detect the temperature rise resulting from any reaction between the protein drop and the ligand drop as they merge. The temperature rise due to the reaction is typically very small and any loss of heat, for example via heat dissipation, can affect the results of the tests.

Evaporation from the samples can lead to heat effects that are significant compared to the enthalpic changes of interest when the samples, e.g. drops, are small. Small drops have a relatively large surface area to volume ratio, so the evaporative flux from the surface area comprises an enthalpic flux that can be large. When the heat flux from evaporation becomes too large compared to the enthalpic change of interest in a measurement, the evaporation becomes a problem. It is valuable to have a device for minimizing evaporation from samples in ultra-miniature calorimeter devices, thereby minimizing this problem, while maintaining the advantage from using small samples, including samples that comprise small drops.

Samples with small dimensions, including samples comprising small drops, provide a way to perform measurements with a minimum of sample volume, which can be important when the measurements use materials that are expensive, precious, or difficult to attain. In drug discovery or life sciences research, samples often are precious, either because they are difficult to make or are derived from a limited resource. Samples are sometimes not even fully characterized, rendering it unfeasible to make more of the material "on demand". For example, the sample could be a naturally occurring extract that is difficult to acquire, or it could be a material available only in a limited quantity in a "library" of compounds derived by combinatorial chemistry methods. Samples with small dimensions, including samples comprising small drops, can also be important when performing measurements on an array. Industry standards for dimensions of arrays specify certain dimensions for each site, and it is desirable to stay within the standards. For example, industry standards for a 96-site microarray for drug discovery applications and automated laboratory instrumentation specify a 9 mm pitch, and the pitch for 384-site and 1536-site microarrays are 4.5 mm and 2.25 mm, respectively. If multiple drops are to be located on a site in such arrays, their size must be correspondingly small. For example, for a known calorimeter device, the drops must have a diameter of about 1 mm or less to fit on the sensing regions of the device.

There is also interest in developing devices other than calorimeters wherein controlling thermal or volumetric changes caused by evaporation is important. Typically the samples in such devices have small dimensions, including samples comprising small drops or comprising liquid patterns in which at least one dimension is small enough for evaporative effects to be important. As examples, miniature devices in which thermal effects are used to actuate or move species therein, or in which precise assays require precise control of sample volume, can be adversely affected by evaporation. Minimizing or preventing such adverse effects is important in improving such devices.

BRIEF DESCRIPTION

A detection system includes a detection device and an anti-evaporation device. The detection device comprises a region configured to merge at least two small drops and to detect a potential signal generated by the merger of the drops. The anti-evaporation device is configured to at least substantially enclose the region and limit evaporation from the region.

An anti-evaporation device for use with a detection device where interactions are undertaken on small sample materials includes a substantially planar member having dimensions to cover at least a portion of a the detection device. At least one extending member extends substantially perpendicular to the planar member and includes a distal end configured to contact the detection device.

A method for detecting a signal includes the following steps: depositing drops of potentially reactive chemical solutions on a detection device within a drop-merging region; placing an anti-evaporation device around the drop-merging region to form a seal around the drop-merging region; merging the drops of potentially reactive chemical solutions; and measuring a signal occurring within the merged solution drops.

BRIEF DESCRIPTION OF THE DRAWINGS

FIG. 1 is a side cross-sectional view of a nanocalorimeter;

FIG. 2 is a plan view of the nanocalorimeter of FIG. 1;

FIG. 8 is a plan view of a frame for a nanocalorimeter array and a humidity source for the nanocalorimeter array;

FIG. 9 is a plan view of the frame disclosed in FIG. 8 showing an alternative humidity source;

FIG. 17 is a top view of the cap of FIG. 16;

FIG. 18 is a side cross-sectional view of another embodiment of a detection device and an anti-evaporation device for use with the detection device;

DETAILED DESCRIPTION

Figure 3:
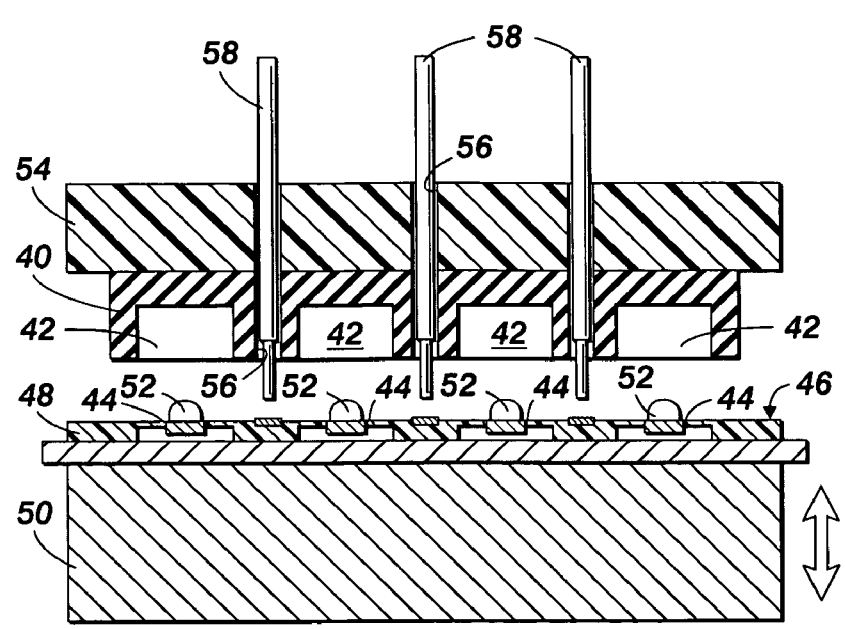
FIG. 3 is a side cross-sectional view of a nanocalorimeter array and a cap for the nanocalorimeter array.

With reference to FIG. 1, this embodiment of a calorimeter 10 includes a membrane or substrate 12 mounted on a support 14. The substrate in the illustrated embodiment is made of a plastic material, such as Dupont Kapton, 12.5 or 25 µm thick. The calorimeter in the illustrated embodiment is used to detect very small enthalpic changes, in the range of nanocalories to microcalories, and is known in the art as a nanocalorimeter or a microcalorimeter. The calorimeter can be part of an assay device, such as a 96-element array. For the 96-element assay device, each site typically includes one calorimeter and has an assay volume ranging from 20 nL to 10 µL.

With reference to FIGS. 1 and 2, drop merging devices, such as electrodes 16, and sensing devices, such as thermometers 18, reside on an upper or first surface 22 of the substrate. The drop merging electrodes 16 can be thin metal films patterned using any thin film deposition process known in the art. The electrodes can range in size from approximately 10 microns to 8 mm on each side and adjacent electrodes that are used together to merge drops can be spaced apart from each other by a gap that can range in size from approximately 1 µm to approximately 500 µm. The thermometers 18 can comprise thermistors that are connected to power sources for actuation and to an external device for displaying, storing and/or manipulating input sensed by the thermometers. In this case, the element 18 comprises the thermistor material having a temperature coefficient of resistance that is high enough to allow measurements of the desired temperature changes, and thermometry is possible when current is passed through the thermistor using the abovementioned power source. Accordingly, for thermistor elements both the thermistor and the current passing through the thermistor are elements of the resistive thermometer 18. A thermally conductive film, such as copper film 24, is disposed on a lower or second surface 26 of the substrate 12 in this embodiment for thermal equilibration across the sensing region. In other embodiments, the thermometers can be other types of temperature-sensing elements, examples including thermocouples, thermopiles of thermocouple junctions, temperature sensitive mechanical elements such as microfabricated cantilevers with a temperature dependent deflection, and other temperature sensitive elements known in the art. Thermometers that sense from a distance, such as infrared temperature detectors, can also be used.

The electrodes 16 are encased with an insulating/dielectric layer (not shown), which may range in thickness from about 0.1 µm to about 25 µm. Examples of suitable materials include silicon oxide, silicon nitride, silicon oxynitride, tantalum oxide or polymers such as parylene (e.g. parylene N, C, D, HT), Dupont Teflon AF, 3M Fluorad, 3M EGC 1700, other fluoropolymers, polysiloxanes, diamond-like carbon or other spin-coated, spray-coated, dip coated, or vapor deposited polymers, or combinations thereof. Drops to be merged are deposited on the electrodes 16. For embodiments where significant lateral motion along the substrate is desired, an upper surface of the dielectric layer is preferably highly hydrophobic if the drops are aqueous-based and preferably highly oleophobic if the drops are oil based, to enhance the ease of motion of the drops along the surface. As an example, a hydrophobic surface may be achieved by using a hydrophobic dielectric layer (e.g. parylene), or by depositing a hydrophobic layer on top of the dielectric layer. Suitable hydrophobic materials typically include Fluorocarbons such as Dupont Teflon AF, 3M Fluorad, 3M EGC 1700, other fluoropolymers, polysiloxanes, diamond-like carbon or vapor or plasma deposited fluorocarbons.

As mentioned above, drops 28 are deposited onto a region having the drop merging electrodes 16 and a sufficiently large voltage difference is applied between two adjacent electrodes 16 so that electrostatic forces cause the drops 28 to move toward one another until they merge. This merger can result in heat being released and the thermometers 18 measure (e.g. sense) this heat. The nanocalorimeter 10 is used to detect heats of reaction corresponding to temperature increases of 1 µ° C. to 10 m° C. To detect such small temperature increases, the signal from the thermometer should be averaged over as long a time as possible (1-30 seconds is desirable) to achieve a large enough signal to noise ratio; however, the signal can only be averaged for as long as the drops retain the heat from any reaction. Dissipation of heat limits the averaging time. When evaporative heat losses exist, they add to the dissipation of heat, shortening the time of the signal. For samples with small dimensions, including samples comprising small drops, the evaporative heat losses can be significant, since the surface area to volume ratio can be large.

Evaporative heat losses can also degrade common mode rejection in calorimeter devices. The common mode rejection refers to rejection of common thermal effects between a sample of interest and a reference. In particular, if the evaporative heat losses are not exactly the same for the sample and reference, then the common mode rejection is less effective. Common mode rejection is used in calorimeters to minimize effects of background drifts in temperature. In particular, in FIG. 2 one pair of drops contains the samples of interest, and the second pair on the second sensing region contains non-reacting reference drops. The reference drops are chosen to closely match the sample drops in all respects except for the actual reaction of interest, so they are closely matched, for example, in size, buffer, and co-solvent. The thermometers on the device are configured to measure the temperature difference between the two regions to effect a measurement with common mode rejection. If evaporative heat losses exist and are not substantially exactly matched for the two regions, for example due to evaporative loss to the environment that is asymmetric, then the common mode rejection is degraded.

Although small sample sizes can lead to problems with evaporation, samples with small dimensions, including samples comprising drops, provide a way to perform measurements with a minimum of sample volume, which can be important when the measurements use materials that are expensive, precious, or difficult to attain. In drug discovery or life sciences research, samples often are precious, either because they are difficult to make or are derived from a limited resource. Samples are sometimes not even fully characterized, rendering it unfeasible to make more of the material "on demand". For example, the sample could be a naturally occurring extract that is difficult to acquire, or it could be a material available only in a limited quantity in a "library" of compounds derived by combinatorial chemistry methods.

Samples with small dimensions, including samples comprising small drops, can also be important when performing measurements on an array. Industry standards for dimensions of arrays specify certain dimensions for each site, and it is desirable to stay within the standards. For example, industry standards for a 96-site microarray for drug discovery applications and automated laboratory instrumentation specify a 9 mm pitch, and the pitch for 384-site and 1536-site microarrays are 4.5 mm and 2.25 mm, respectively. If multiple drops are to be located on a site in such an array, their size must be correspondingly small. For example, for the calorimeter embodiment shown in FIGS. 1 and 2, the drops must have a diameter of about 1-2 mm or less to fit on the merging/sensing regions of the device, if each individual device is to have a 9 mm or smaller pitch. The device preferably fits within the 9 mm pitch of an industry-standard 96-site array, leaving only limited space for the drops shown in FIGS. 1 and 2, as the pads, isolation areas, and two sensing regions all require some of the space available for each individual device. There is clearly an advantage to matching the standards for dimensions of microarrays. For example, matching the standards allows for easier integration with other tools available for automated laboratory instrumentation, which is important both in research applications and in drug discovery efforts that utilize medium and high throughput measurements.

Electrical connections to the thermometer and drop merging electrodes can be made using the pads 30 in FIG. 2. For example, these pads can be contacted with pogo pins to establish electrical connections. The pogo pins can be chosen for low thermal conduction in cases where that is important.

Other types of ultra-miniature calorimeters exist that can be conceived to use small samples. See for example U.S. Pat. Nos. 6,079,873; 6,096,559 and 6,193,413, U.S. Pat. Nos. 6,545,334B2, 6,380,605B1. The teachings in this disclosure can be applied to these and other embodiments of ultra-miniature calorimeters, in addition to the embodiment of a calorimeter described in FIGS. 1 and 2.

The devices and methods disclosed are particularly useful when the surface area for evaporation is large enough compared with the sample volume to cause evaporative heat fluxes that, when integrated over the time that a signal is sampled, are comparable to the heat capacity (mass×specific heat) of the sample. The large ratio of surface area to volume can occur with small samples (typically less than 50 μL in volume), as well as with thin films that wet a substrate or are free standing.

The teachings of this disclosure can also be applied to other types of devices where thermal or volumetric effects are important and controlling the thermal effects or volume changes resulting from evaporation are important, even when the purpose of the device is not to directly detect temperature changes. For example, the teachings of this disclosure can be applied to miniature devices (typically used for operations comprising small samples less than 50 μL in volume) in which thermal effects are used to cause a desired change in state, or in which thermal effects are used to actuate or move samples or species therein, or in which precise assays require precise control of sample volume. Examples of measurements that are anticipated include assays comprising fluorescence detection, radiolabel detection, electrochemical detection, surface plasmon resonance measurements, acoustic detection of changes at a surface, and DNA assays. In many such assays, concentration changes that would accompany evaporation of samples are undesirable because the precision of the assay requires well-defined concentrations. Otherwise, unwanted or unexpected reactions could occur or increase in extent, examples of such undesirable reactions including non-specific binding or low affinity binding. Also, in reactions involving multiple species and steps, a change in concentration caused by evaporation could alter the balance of reactions in a way that diminishes the quality of the assay.

In embodiments, the teachings of this disclosure can be applied when drops, or other discrete sample elements, are brought into contact to initiate an interaction, and it is important to detect a transient signal associated with that interaction. For example, in the calorimeter in FIGS. 1 and 2, drops are merged and mixed, and the difference between the temperatures of the combined sample drops relative to the combined reference drops is measured. This signal then corresponds to the presence or absence of some interaction of interest. This temperature difference is transient because, given enough time, any heat from interactions in the drops dissipates to the surroundings. When evaporation can alter the transient signal, using appropriate caps as described in this disclosure to limit the rate of evaporation is anticipated.

In embodiments, evaporation may cause an undesirable transient. In that case, caps as described in this disclosure can be used to minimize, or even substantially eliminate, such transients. For example, it may be undesirable to have evaporation in measurements of fluorescence or radioactivity. A transient signal can be undesirable when the signal, such as fluorescence, is too short or if it changes too rapidly due to evaporation, or if the drop substantially disappears due to evaporation before having enough time for quality detection (i.e. decent signal-to-noise). For small drops exposed to the surroundings without a device to limit evaporation, the drops tend to evaporate in minutes, or even seconds, whereas the caps disclosed here slow down the evaporation significantly, allowing more time for detection of such signals. Slowing down the evaporation also slows down the corresponding changes in concentrations of fluorophores or radio-labeled species.

Thermal dissipation in the embodiment described by FIGS. 1 and 2 occurs through four different channels: conduction across the supporting medium, conduction through the electrical interconnect, conduction through the surrounding environment and evaporation. The characteristic time for dissipation by evaporation of the heat of reaction from a drop can be estimated by using the equation $$\tau = \frac{mc_P \Delta T_{rxn}}{\Delta H_{vap}(\dot{m} - \dot{m}_{ss})}$$

where m is the mass of the drop, $c_p$ is the heat capacity at a constant pressure, $\Delta T_{rxn}$ is the temperature rise due to the reaction, $\dot{m}$ is the rate of evaporation, and $\dot{m}_{ss}$ is the rate of evaporation in the absence of a reaction. Assuming the flux of water vapor away from the drop is diffusive, then the rate of evaporation can be estimated by using the equation $$\dot{m} = AD\nabla c$$

where A is the area of the drop exposed to the vapor phase, D is the diffusivity of water molecules in the vapor phase (for the case where the drops are aqueous), and $\nabla c$ is the gradient of the concentration of water vapor. In this example, convective motion of the vapor phase is minimized or eliminated, but it can be appreciated that in other embodiments the movement of the water vapor may not be totally diffusive. Where the concentration of water vapor at the surface of the drop equals the saturation concentration at the temperature of the drop, then $$\nabla c = \frac{MW}{RT} \frac{dP_{sat}}{dT} \nabla T$$

where MW is 18 g/mol, the molecular weight of water, R is the gas constant, T is the temperature, and $P_{sat}$ is the saturation vapor pressure at a given temperature T. An appropriate length scale for estimating the magnitude of the gradients is the radius of the drop, in the absence of significant convection. Combining the above equations and recognizing that $(c-c_{ss})$ corresponds to $\Delta T_{rxn}$ yields $$\tau = \frac{mc_P RT a_{drop}}{\Delta H_{vap} ADMW \frac{dP_{sat}}{dT}}$$

where $a_{drop}$ is the drop radius.

For a 400 nL drop in air with a density of 1 $g/cm^2$, $C_p=1$ cal/g/° C., $a_{drop}=576$ μm (a hemispherical drop), $\Delta H_{vap}=576$ cal/g, $A=2\pi a_{drop}^2$, and $D \approx 0.2$ $cm^2$/sec, then $\tau=4$ seconds at 37° C., and $\tau=25$ seconds at 5° C. As can be seen, operation at higher temperatures makes signal detection more difficult because of the shorter integration time. To limit thermal dissipation that occurs via evaporation, an anti-evaporation device such as a cap and/or frame can be placed over a sensing region of a calorimeter, such as the one described above, or a calorimeter array, which will be described in more detail below. The anti-evaporation device serves to increase the concentration of water in the vapor phase, but it also serves to reduce convection in the vapor phase in many cases.

With reference to FIG. 3, an elastomeric cap 40 includes a plurality of cavities 42 that at least substantially, and can entirely, enclose sensing regions 44 that are disposed on or adjacent an upper surface 46 of a calorimeter array 48. The calorimeter array 48 can include a plurality of calorimeters, such as the calorimeter described with reference to FIGS. 1 and 2. The sensing regions 44 and calorimeter, array 48, however, are not limited to only calorimeters having electrodes and thermometers where the electrodes are used to move liquid drops. The sensing regions 44 can include area(s) on an integrated device where a drop 52 containing the analyte(s) is in direct communication with a microfabricated calorimeter. For example, the U.S. Patents and U.S. patent applications that have been incorporated by reference, disclose such microfabricated calorimeters and the sensing regions include the area where the analyte(s) is/are deposited and the temperature measurements are made. Accordingly, the calorimeter array 48 described working with the caps and/or anti-evaporation devices described below can be any such microcalorimeter or nanocalorimeter where it is desirable to control the evaporation of the analyte. The calorimeter array in FIG. 3 can mount to a heat sink 50, which can be a copper block.

The cap 40 in the embodiment illustrated in FIG. 3 can be made from an elastomeric polymer such as poly(dimethylsiloxane) ("PDMS"). The elastomeric material forms a seal when pressed against the upper surface 46 of the calorimeter array 48 to at least substantially inhibit mass transport from the fluid drops 52 out of the cavities 42. Pogo pins 58 can be inserted through the cap 40 without breaking the seal around the cavities 42 in order to provide electrical connections to pads on array 48, for example for connections to drop merging devices 16 and sensing devices 18 illustrated in FIGS. 1 and 2. Also, vias (not shown) can be made through the elastomeric cap 40 to provide electrical connections to electrical components of the calorimeter array 48, for example the drop merging devices 16 and sensing devices 18 illustrated in FIGS. 1 and 2.

Each drop 52 is typically about 250 nl and has a height of about ½ mm in one embodiment of a nanocalorimeter method. For an embodiment of the design illustrated in FIG. 3, each cavity 42 has a height of about 3 mm, which allows air between an inside surface of the cavity and the drop 52 to thermally isolate the drop from the cap 40; however, in an alternative embodiment the drop can contact an inner surface of the cavity. The drop size might change and the dimensions of the cavity can be changed to accommodate a drop having different volume. In embodiments with drop merging electrodes, each cavity 42 also has a length and width to accommodate at least one set of drop merging electrodes and a respective thermometer, and may be large enough to accommodate several drop merging electrodes and thermometers. In other embodiments, each cavity can accommodate an area where a plurality of drops are merged. A cavity that accommodates a sensing region having multiple electrodes and thermometers and/or multiple drops may be desirable where multiple trials are to be performed on the same type of sample for averaging. A sensing region can include an area where multiple operations are performed. In yet other embodiments, calorimeters do not employ electrodes to move drops, but instead use other devices and/or methods, such as microfluidics or injection of droplets using drop dispensing methods known in the art.

The cap 40 can attach to a more rigid cover plate 54 at a side opposite the cavities 42. The plate 54 can provide a surface upon which a force can be applied to press the cap 40 against the upper surface 46 of the calorimeter array 46. Passages 56 are provided through the cap 40 and the plate 54 for receiving members, such as pogo pins 58. The passages 56 do not extend through the cavities 42.

Figure 4:
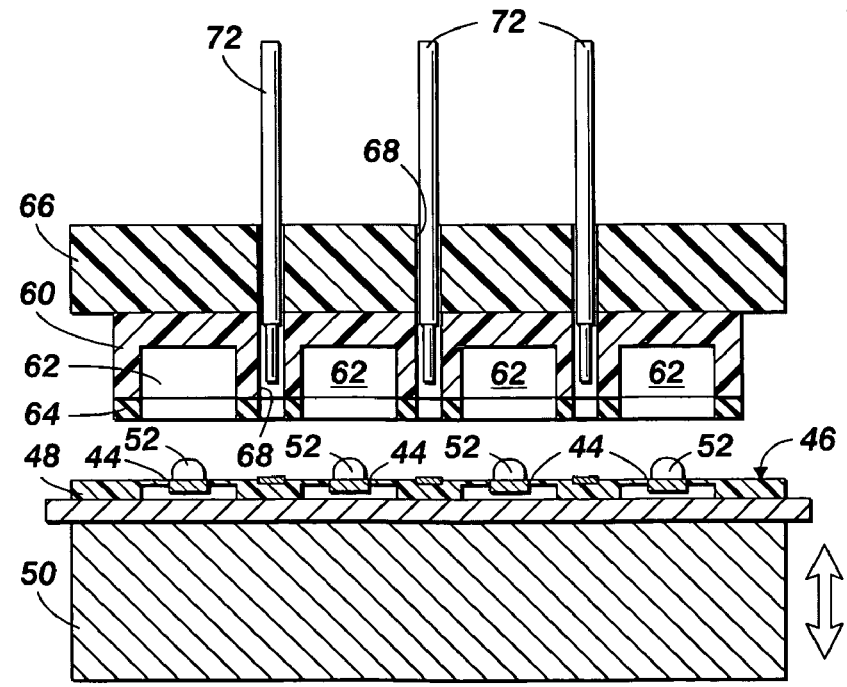
FIG. 4 is a side cross-sectional view of a nanocalorimeter array and another embodiment of a cap for the nanocalorimeter array.

FIG. 4 illustrates an alternative embodiment of a cap 60 for use with the calorimeter array 48. The cap 60 can be made of a rigid material, such as a rigid plastic such as PCTFE, and include a plurality of cavities 62 and a gasket or seal 64 that at least substantially, and can entirely, enclose the sensing region 44. The gasket can be made from an elastomeric polymer, such as PDMS or Gel-Pak Gel-Film™ materials, or another membrane that seals against the upper surface 46 of the calorimeter array 48 to at least substantially inhibit evaporation of the drops 52. Like the embodiment disclosed in FIG. 3, electrical connections to the drop merging devices, sensing devices and/or other components can be made by vias (not shown) through the cap 60 and/or gasket 64 or by pogo pins 72. Likewise, the cavities 62 can take a similar configuration to the cavities described with reference to FIG. 3.

The cap 60 illustrated in FIG. 4 can attach and/or contact a cover plate 66 and passages 68 are provided through the plate 66, cap 62 and gasket 64 for receiving pogo pins 72. The passages do not extend through the cavities 62.

Figure 5:
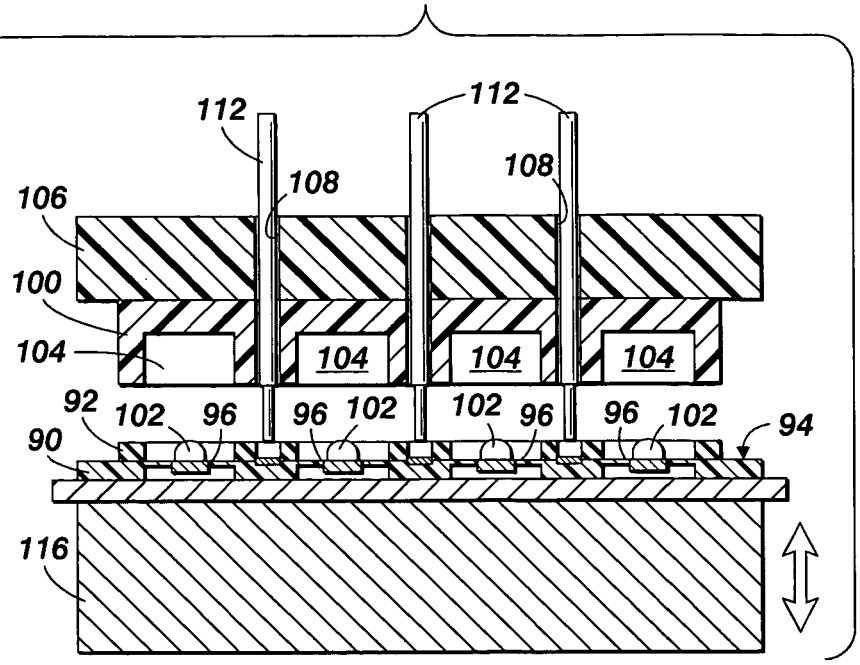
FIG. 5 is a side cross-sectional view of another embodiment of a nanocalorimeter array and a cap for the nanocalorimeter array.

FIG. 5 illustrates a calorimeter array 90 similar to the calorimeter array illustrated in FIGS. 3 and 4, but having a gasket 92 formed on an upper surface 94 around a sensing region 96. The gasket can be formed using a variety of methods, such as screen printing, photolithography, or molding. The gasket can either be formed in place or formed separately and then fastened to the array 90. The gasket can be structured to allow access to electrical connections and the sensing region 96.

A cap 100 made of a rigid material is pressed down on the gasket 92 to provide environmental isolation for drops 102 deposited on the calorimeter 90. Similar to the embodiment illustrated in FIGS. 3 and 4, the cap 100 includes a plurality of cavities 104 that at least substantially surround the sensing regions 96. The cap 100 can contact and/or attach to a plate 106 upon which a force can be applied to press the cap 100 against the gasket 92. Passages 108 are provided through the plate 106 and the cap 100 to receive pogo pins 112. The calorimeter array 90 can also mount on a heat sink 116, similar to the calorimeter 48 described with reference to FIGS. 3 and 4. One advantage of using a rigid material for the cap 100 is to minimize the absorption of water by the cap. Elastomeric caps, such as PDMS caps made from Sylgard 184, can absorb water to a larger degree than many rigid materials, examples of such rigid materials including Teflon and related materials, Delrin, PCTFE, polypropylene, and polyethylene.

Even with the caps 40, 60 and 100 described above, evaporative cooling may take place from condensation or where the cap absorbs vapor. Addition of a separate vapor source within the region covered by the cap can further minimize evaporative heat flux from the drops due to condensation and/or the cap absorbing vapor. The addition of a source of vapor within the region covered by the cap can be accomplished by the addition of a liquid containing region or a porous material that can hold liquid, such as a polyacrylamide gel or cellulose wick, to a portion of the cap. The liquid for the vapor source is chosen to match the characteristics of the analyte solutions, e.g. buffer concentrations and concentrations of co-solvents such as DMSO, in order to match the corresponding vapor phase concentrations as close as is necessary. In some cases it may be advantageous to supply a non-condensing gas of low thermal conductivity as well, such as xenon or argon, to the region covered by the cap.

Figure 6:
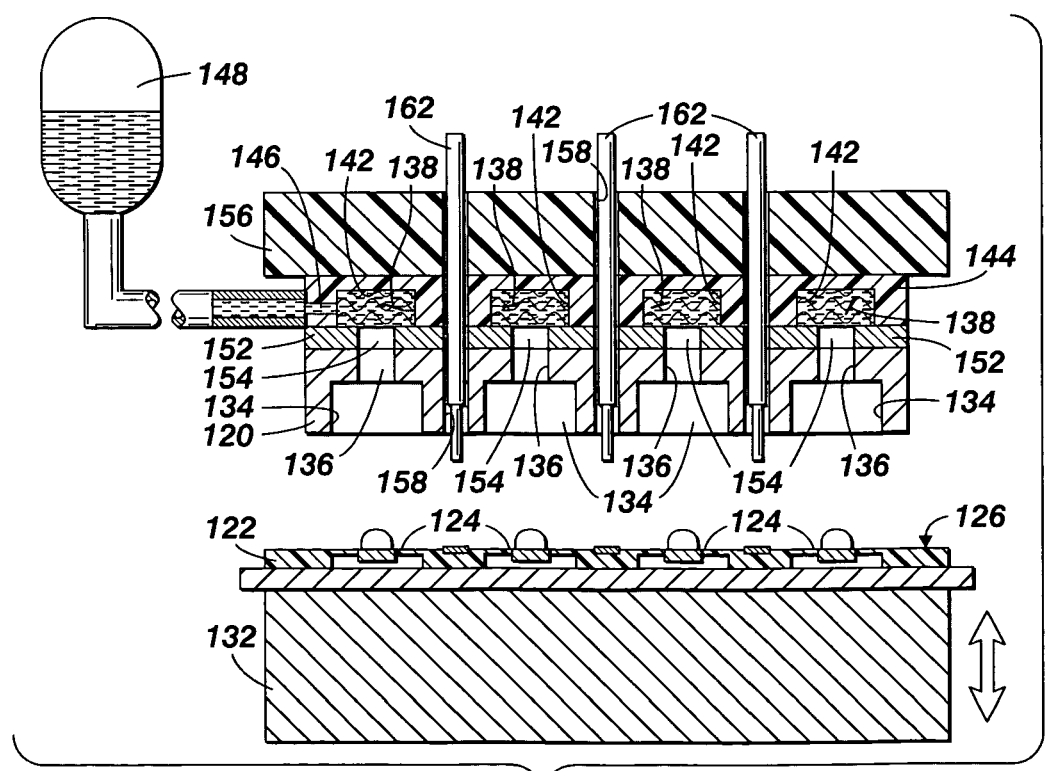
FIG. 6 is a side cross-sectional view of a nanocalorimeter array and another embodiment of a cap that communicates with a fluid source.

With reference to FIG. 6, a cap 120 contacts a calorimeter array 122, which can be similar to the calorimeter arrays described. The calorimeter array 122 includes a plurality of sensing regions 124 disposed on an upper surface 126 and is mounted to a heat sink 132. The cap 120 can be made from the materials described above and includes a plurality of cavities 134 that surround the sensing regions 124. The cap 120 also includes a plurality of openings 136, each opening extending through the cap and being in communication with a respective cavity 134, for supplying humidity to the cavity 134.

For supplying humidity to the cavity 134, a saturated felt 138, or other suitable wetted material, can be disposed in a liquid containing reservoir 142 defined in a plate 144 that contacts the cap 120. Passages 146 are provided in the plate 144 to allow the liquid containing reservoirs to communicate with one another. A fluid source 148 communicates with the passages 146 to supply fluid to the felt 138. A seal or gasket 152, similar to the gaskets and/or seals described above, is interposed between the plate 144 and the cap 120, to prevent, at least substantially, any vapor from leaving between the plate 144 and the cap 120. Passages 154 are provided in the gasket 152 so that the saturated felt 142 is in communication with the cavity 134.

An additional plate 156 contacts the plate 144 containing the liquid containing reservoirs 142, similar to the plates described above, so that pressure can be applied to the cap 120 to seal the cap to the calorimeter array 122. Passages 158 are also provided to receive pogo pins 162 to provide electrical connections to the calorimeter 122.

Additionally, each reservoir 142 can have a wick disposed therein. The wicks may all be independent, i.e. not connected to one another. In this case, each wick is wetted individually before a measurement. This allows for use a different liquid to wet the wick for each site, which can have advantages if the buffer or co-solvent differs from site to site. When the wicks are not connected to one another, the plate 144 becomes unnecessary, since the wicks can be located in the upper part of the cavities 134, for example in the openings 136. In this case it can also be an advantage for the openings 136 to be sealed off at the top of the cap, helping to prevent the wick from drying rapidly.

Figure 7:
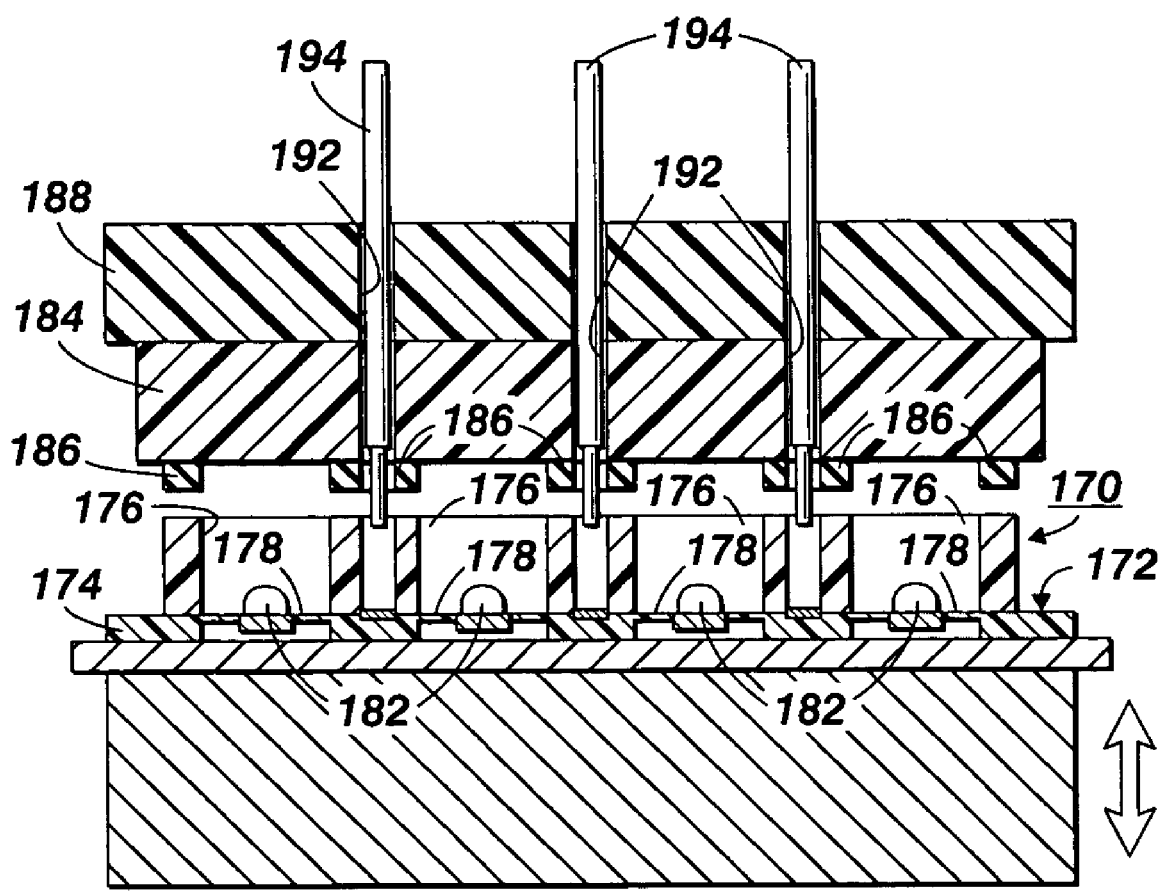
FIG. 7 is a side cross-sectional view of another embodiment of a nanocalorimeter array and a cap for the nanocalorimeter array.

FIG. 7 illustrates another embodiment where a cap structure minimizes evaporative heat fluxes from sample drops 182. In this embodiment, a solid frame 170 extends upwardly from an upper surface 172 of a calorimeter array 174 to form a plurality of wells 176 that at least substantially surround sensing regions 178. In this embodiment, each well 176 measures about 3 mm deep, which is a similar dimension to the depth of the cavities described above, and the drops are 250-500 nL in volume. The frame 170 may minimize evaporation of drops between the time of drop 182 placement and when a cap 184 contacts the frame, as compared to a calorimeter without any wells, as it minimizes convection right around the drop and serves to hold in vapor becoming saturated by the liquid in the drop.

The cap 184 and solid frame 170 can be made of a solid material, e.g. polypropylene or Dupont™ Teflon® or PCTFE, to minimize any vapor transmission into the cap. A soft gasket or seal 186 can attach to and extend down from the cap 184 to be sandwiched between the hard frame 170 and the hard cap 184. The gasket 186 can be made from a soft elastomer, e.g. PDMS, a Gel-Pak Gel-Film™ material, or other suitable material. A plate 188 can attach to and contact the cap 184. Force can be applied to the plate 188 to seal the cap 184 and gasket 186 to the frame 170. Passages 192 can be provided for receiving pogo pins 194 for electrical connections to the array 174.

With reference to FIGS. 8 and 9, a frame 200 for use with a cap 184 described with reference to FIG. 7, or other suitable cap described above, is shown. The frame 200 can be made of a solid plastic and include a plurality of wells 202 that surround a sensing region on a calorimeter array. A liquid containing region 204 can occupy a portion of the well 202 to provide vapor to the sensing region. In the embodiment depicted in FIG. 8, a wick 208 is disposed in the liquid containing region. The wick 208 can be wetted with the same equipment used for drop deposition and can be supported on the calorimeter array. The wick 208 can be wetted with a liquid chosen to match the characteristics of the analyte solutions, e.g. buffer concentrations and concentrations of co-solvents such as DMSO. The purpose is to match the vapor composition in equilibrium with the wick liquid and the vapor composition in equilibrium with the sample drops. In some cases it may be advantageous to also supply a noncondensing gas of low thermal conductivity, such as xenon or argon, to the regions surrounded by the frame 200.

With reference to FIG. 9, instead of the wick, a buffer drop 212 can be deposited in the liquid containing region 204. The buffer drop can be a solution, such as a buffer solution, chosen to match the characteristics, including co-solvents such as DMSO, of the analyte drops 216 (depicted only in FIG. 9), similarly to the liquid chosen to wet the wicks in FIG. 8. As seen in both FIGS. 8 and 9, openings 218 can be provided in the frame 200 for receiving pogo pins (not shown in FIGS. 8 and 9).

Figure 10:
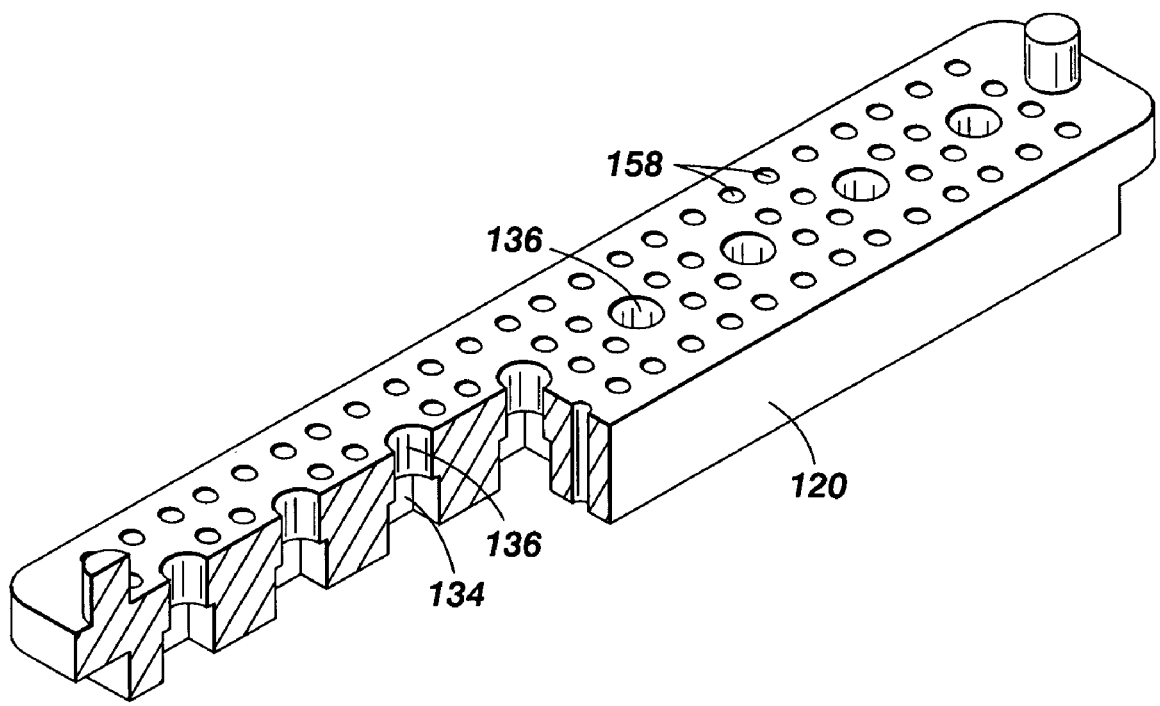
FIG. 10 is top perspective view, partially broken away, of the cap illustrated in FIG. 6 that covers one row of a nanocalorimeter array.
Figure 11:
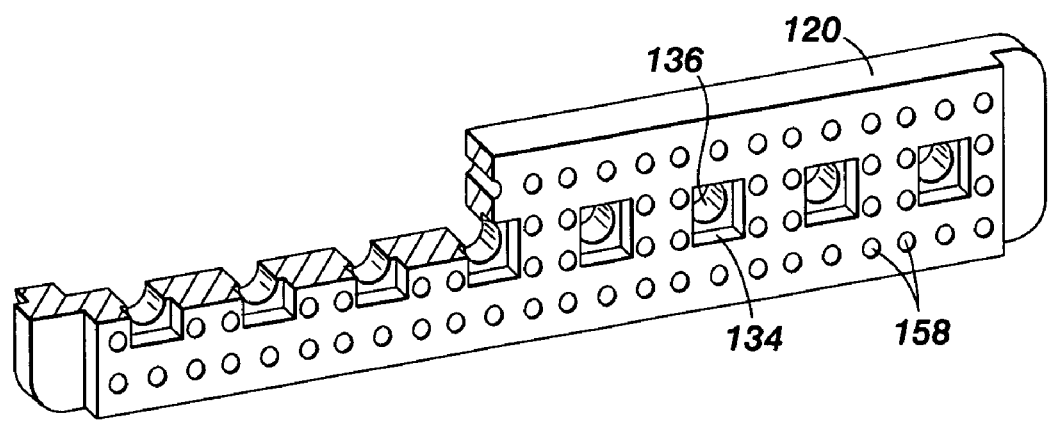
FIG. 11 is a bottom perspective view, partially broken away, of the cap of FIG. 10.

With reference to FIGS. 10 and 11, an example of a cap 12b described with reference to FIG. 6 is shown. In FIG. 6, the cap as shown covers all of the sensing regions in the calorimeter array, but in some cases it may be sufficient to cover only a subset of sensing regions at a time. FIGS. 10 and 11 show a cap that covers only a single row in an 8×12 array. In some cases this is sufficient, for example, if the array is only measured one row at a time, then a cap covering only one row at a time is sufficient. In other cases, it may be easier to implement a design having multiple caps that cover the array, such as one cap per row, rather than fabricating and assembling a single cap for the entire array. If a single cap for the entire array is to be used, then the designs in FIGS. 10 and 11 can readily be extended to that case. FIGS. 10 and 11 show cut-away views of four of the cavities in the cap (the four cavities on the left) for illustrative purposes. This sectional view is depicted in order to illustrate more detail, and it is understood an actual cap does not have this section removed.

Figure 12:
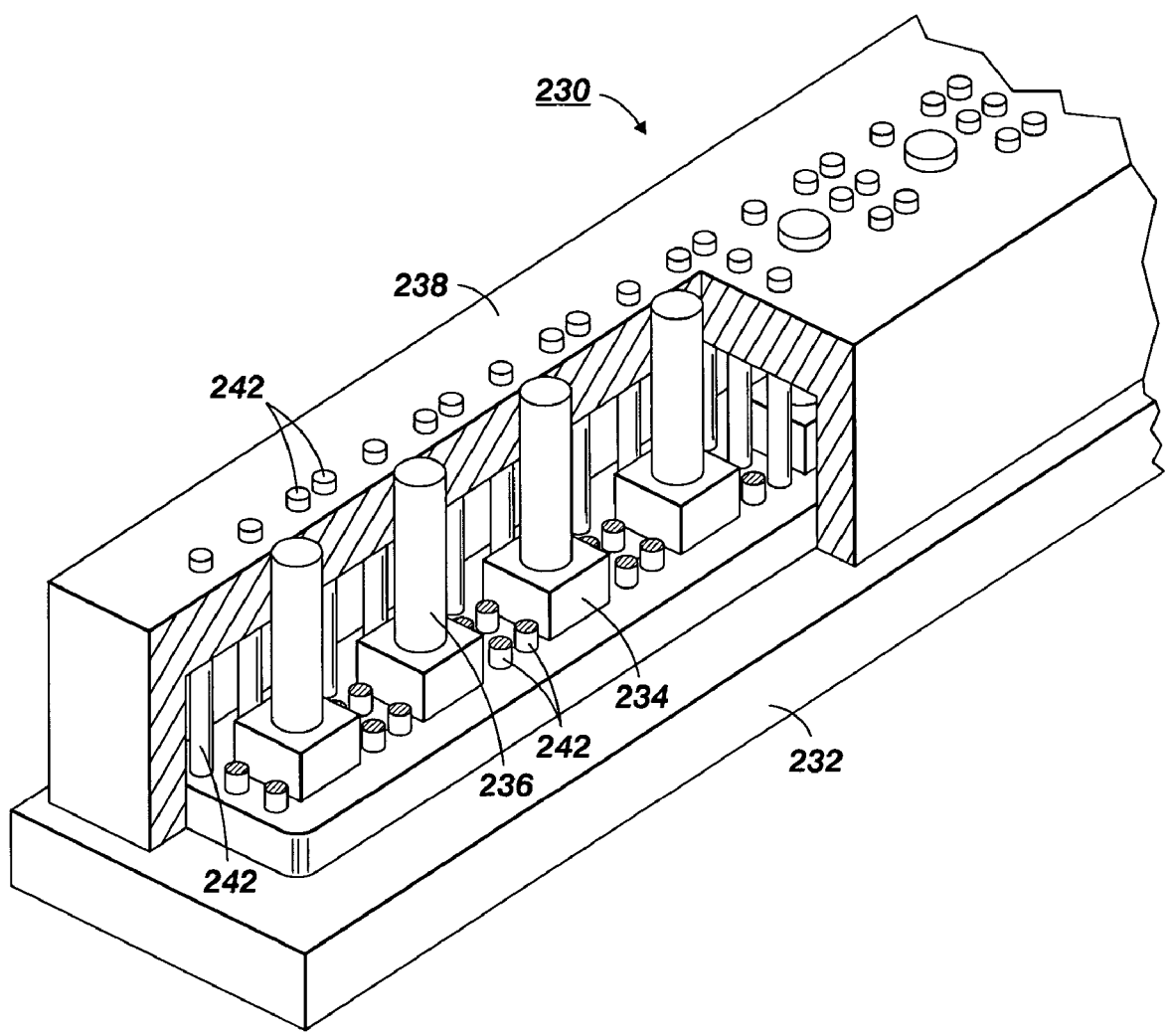
FIG. 12 is a top perspective view, partially broken away, of a molding apparatus used to manufacture the cap disclosed in FIG. 10.

FIG. 12 illustrates a molding apparatus 230 for making the cap 120. The molding apparatus 230 includes a base 232 upon which a plurality of box-shaped members 234 are mounted to form the cavities 134 (FIG. 11). The box-shaped members 234 can be replaced with other structures should a change in the shape or dimensions be desired. Rods 236 extend upwardly from the box-shaped members 234 and through a cover 238 of the molding apparatus. The rods 236 are used to form the passages 136 (FIG. 10) that allow for communication with a humidity source. Spaced from the box-shaped members 234, thinner rods 242 extend upwardly from the base 232 and through the cover 238. These rods 242 form the passages 158 (FIG. 10) for the pogo pins 162 (FIG. 6). A suitable material, e.g. reagents or precursors for an elastomeric material, or material for injection molding of a rigid plastic cap, is placed into the molding apparatus to manufacture the cap 120. For example, a PDMS cap can be made by mixing the base and curing agent of a Sylgard® 184 silicone elastomer kit in the appropriate ratio (generally 10:1 by weight), deaerating, and injecting into the mold, followed by curing.

Figure 13:
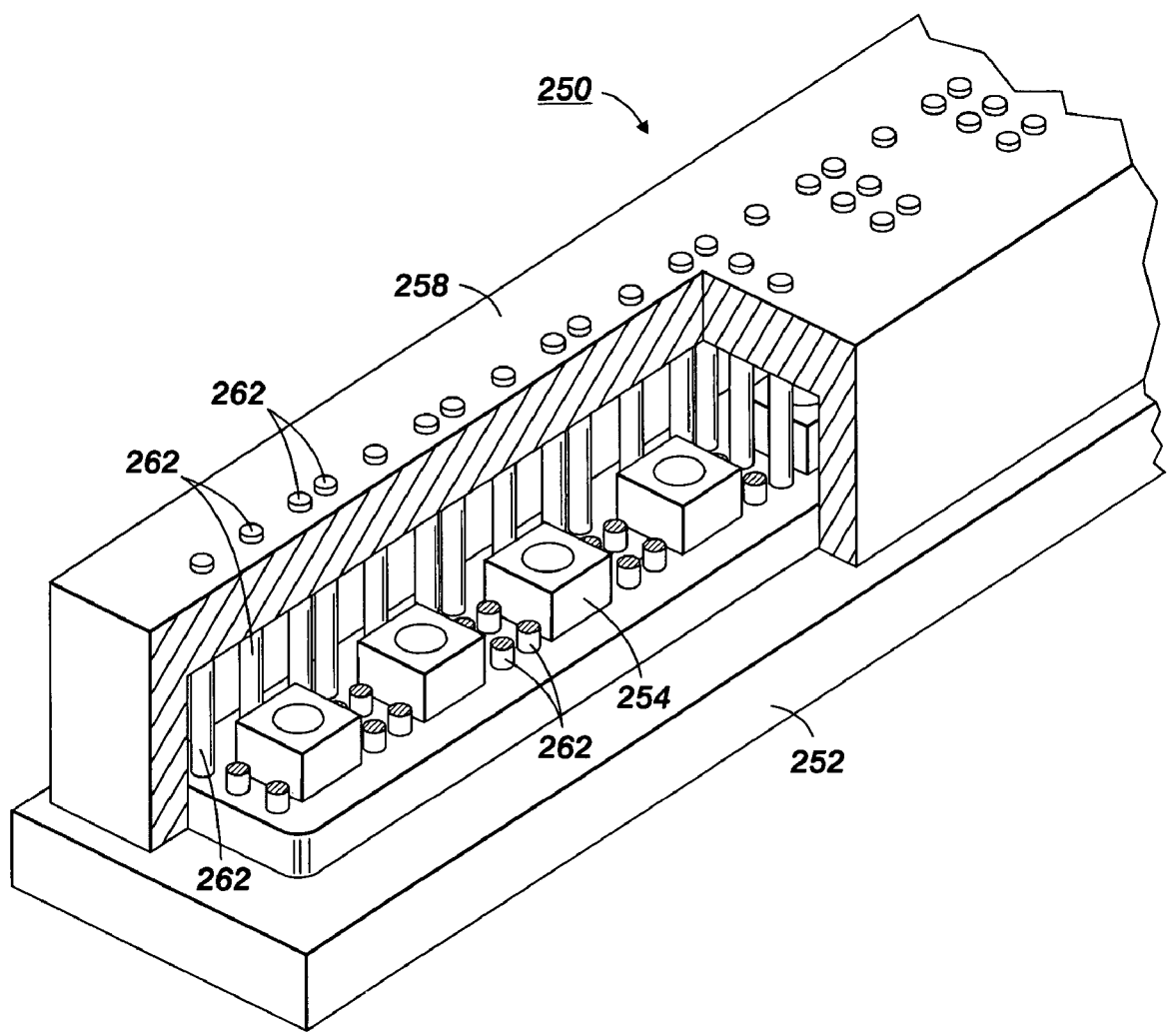
FIG. 13 is a top perspective view, partially broken away, of a molding apparatus for manufacturing the cap disclosed in FIG. 3.

FIG. 13 illustrates a molding apparatus 250 for making the cap 40 illustrated in FIG. 3. The molding apparatus 250 includes a base 252 upon which a plurality of box-shaped members 254 are mounted, similar to the apparatus illustrated in FIG. 12. The molding apparatus 250 in FIG. 13, however, does not include the rods to form passages to allow for communication with a humidity source. Instead, a cover 258 mounts to the base 252 and only rods 262 to form passages to receive pogo pins extend from the base.

As with FIGS. 10 and 11, FIGS. 12 and 13 show embodiments for molds to make caps that cover one row of sensing elements. These designs are readily extended to make a cap structure that covers more sites on an array, or even an entire array. Alternatively, they can be simplified to make caps that cover fewer or only one site if desired.

Figure 14:
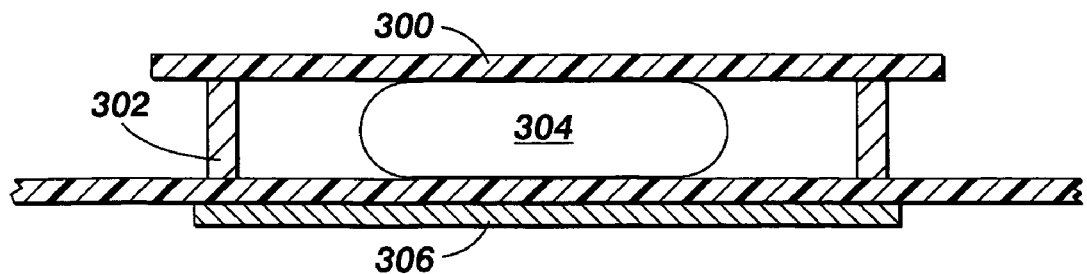
FIG. 14 is a cross-sectional view of another embodiment of a nanocalorimeter array and a cap.

FIG. 14 illustrates another embodiment of an anti-evaporation device for use with a nanocalorimeter. A cover, or cap, 300 is supported by several posts 302, creating a tent-like structure over the drops 304 that are positioned over a sensing region 306. As seen in FIG. 14, the cap 300 is positioned over the sensing region 306 a distance where the drop is in contact both with the sensing region and the cap. The drops 304 are injected from sides, in this embodiment the sides can be open, and capillary forces drive the drops under the cap 300. The force of drop injection can also be used to assist the movement of the drop to a desired location under the drop cover. The cap 300 can be made from any of the materials described above that are used for the caps described above. The cap 300 can also cooperate with a cover plate (not shown) similar to the caps described above.

Figure 15:
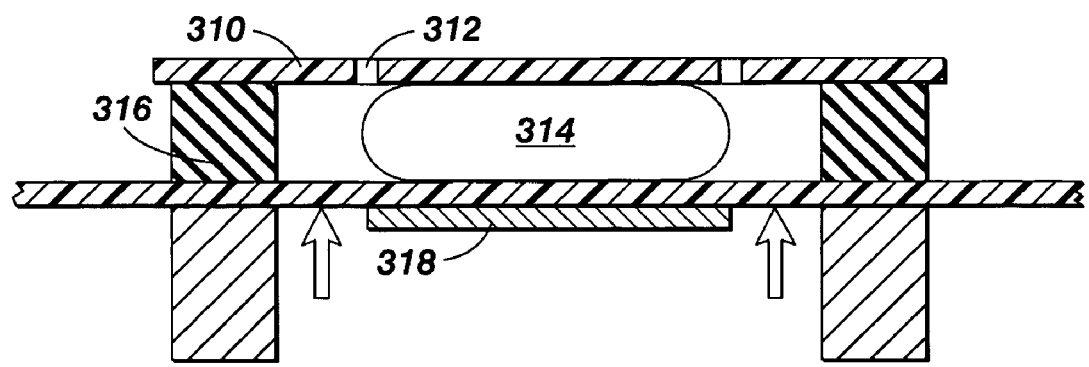
FIG. 15 is a cross-sectional view of another embodiment of a nanocalorimeter array and a cap.

FIG. 15 discloses yet another embodiment. In this embodiment a cap 310 includes a plurality of openings 312 through which drops 314 are injected. The cap 310 is supported by a plurality of supports 316 over a sensing region 318. In this embodiment, the direction of the drop injection determines the location of the drop 314. The cap 310 and supports 316 can be made from any of the materials described above.

Figure 16:
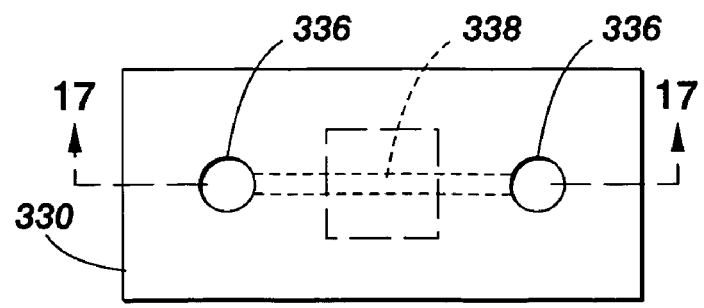
FIG. 16 is a cross-sectional view of another embodiment of a nanocalorimeter array and a cap.

FIGS. 16 and 17 disclose yet another embodiment of an anti-evaporation device for use with a nanocalorimeter. A cap 330 is disposed on a nanocalorimeter array 332 including a sensing region 334 to cover the sensing region. Openings 336 are provided in the cap 330 through which drops (not shown) are disposed. A fluidic channel 338 is provided in the cap 330. In this embodiment, the cap 330 can be fabricated from an elastomeric polymer, such as PDMS and the openings 336 and the fluidic channels 338 guide the droplets.

FIG. 18 discloses yet another embodiment of a system that includes an anti-evaporation device for use with a testing device, for example a nanocalorimeter. In this embodiment, a cap 340 includes a plurality of cavities 342a-c (only three cavities are numbered, however the cap can include more cavities). In this embodiment, one of the cavities 342b can at least substantially, and can entirely, enclose a sensing region 344 disposed on or adjacent an upper surface 346 of a detection device, such as a calorimeter array 348. The sensing region 344 can include area(s) on an integrated device where a drop 352 containing the analyte(s) is in direct communication with a microfabricated calorimeter. The other two cavities 342a and 342c, as well as other cavities that are not depicted, can enclose a region upon which a sacrificial drop 354 is placed. By positioning the sacrificial drops 354 adjacent the sensing region 344, which contains the analyte drops 352, a high humidity environment is formed near the sensing region. By placing a high humidity environment next to the cavity 342b where a signal is being detected, evaporative effects are lessened because water vapor is less able to leak from cavity 342b between the cap 340 and the upper surface 346 of the nanocalorimeter array 348, for example if the seal between the two was not completely impervious.

The system described in FIG. 18 may be useful for several reasons. First, the area of the cavities 342a-c is limited and it may be difficult to find space for a sacrificial, or buffer drop (such as buffer drop 212 in FIG. 9). If a wetted wick, such as the wetted wick 138 depicted in FIG. 6, is used, changing to a different liquid to wet the wick is difficult because the old material has to be removed from the wick. The system described in FIG. 18 also better decouples the temperature of the sacrificial drops 354 from the temperature inside the cavity 342b, where the detection is taking place, allowing faster equilibration. The system described in FIG. 18 also avoids the problem that a liquid source (wick 208 in FIG. 8 or sacrificial drop 212 in FIG. 9) that is not symmetrically placed inside the cavity where sensing and/or detection is taking place or is not at the right temperature can limit the effectiveness of common mode rejection. Liquid sources outside of the cavity where sensing and/or detection is taking place can also perturb the symmetry needed for common mode rejection, but if these liquid sources are there to counteract imperfect seals, then their perturbation of the needed symmetry is expected to be less than a liquid source (wick or sacrificial drop) inside the cavity, at least for reasonable but imperfect seals.

Figure 19:
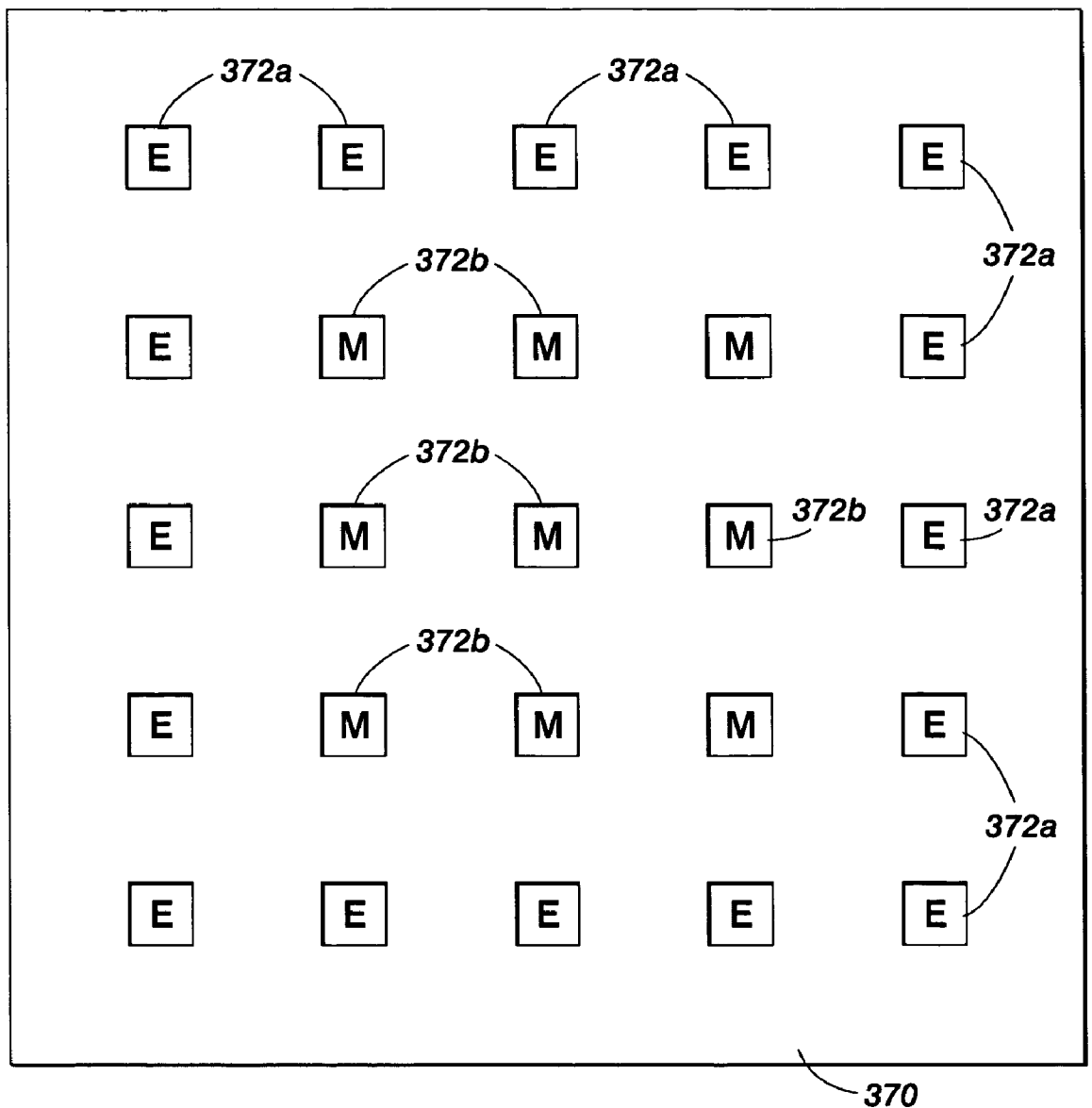
FIG. 19 is a plan view of another embodiment of an anti-evaporation device for use with a detection device.

FIG. 19 discloses yet another embodiment of a system that includes an anti-evaporation device for use with a testing device, for example a nanocalorimeter. In this embodiment, an anti-evaporation device 370 can be placed onto a detection device, such as those described above. The anti-evaporation device includes a plurality of wells, or cavities: external cavities 372a and measurement cavities 372b. The external cavities 372a enclose regions where a sacrificial drop is placed to create separate high humidity regions similar to the embodiment described in FIG. 18. In FIG. 19, the external cavities 372a in which sacrificial drops are placed are positioned around the outer periphery of an array and are isolated from measurement cavities 372b where detection and/or drop merging is taking place. For the internal measurement cavities that are only surrounded by other measurement cavities, there would be analyte drops in both measurement cavities and their partial pressures would equalize. For the measurement cavities next to the external cavities, the partial pressure is equalized with that external cavities as in the example described above with reference to FIG. 18. In another example, an 8×12 array of measurement cavities would be surrounded by 44 external cavities. Many other alternative configurations are also contemplated. A cap, or lid, (not shown) similar to those described above, can be placed on the anti-evaporation device 370.

Figure 20:
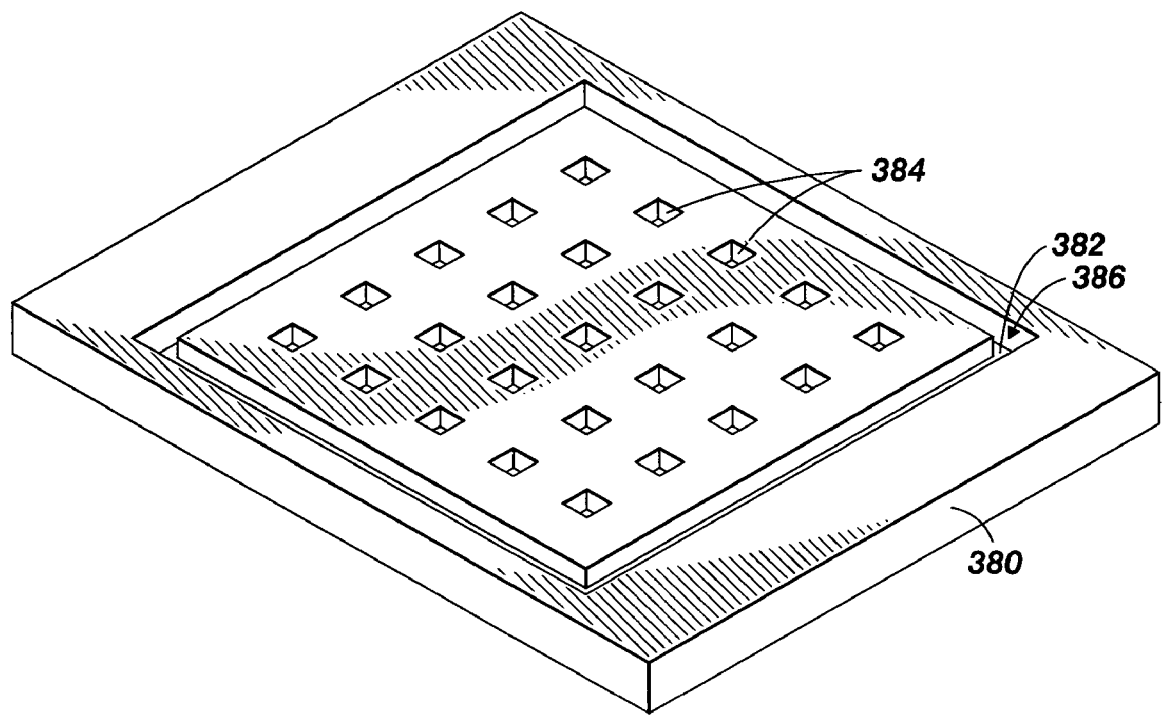
FIG. 20 is a perspective view of another embodiment of a detection device and an anti-evaporation device for use with the detection device.

FIG. 20 discloses yet another embodiment of a system that includes an anti-evaporation device for use with a testing device. In this embodiment, an anti-evaporation device 380 can be placed onto a detection device 382, such as those described above. The anti-evaporation device 380 includes a plurality of measurement cavities 384 (a 5×5 array is shown, but the array can take a number of different configurations) that each at least substantially surround a sensing region and a channel-shaped cavity 386 that at least substantially surrounds the measurement cavities. In this embodiment, the analyte drops are merged on a sensing region that is surrounded by the measurement cavities 384. A liquid source is located in the channel-shaped cavity 386. In alternative embodiments, the channel shaped cavity can run between adjacent measurement cavities in a sort of serpentine or grid-like pattern. Similar to the embodiment depicted in FIG. 19, a cap, or lid, can be placed on top of the anti-evaporation device 380.

As indicated above, the many different embodiments of anti-evaporation devices can be used in conjunction with many different detection devices. These detection devices can include devices that measure heat, as well as devices that detect fluorescence, radioactivity and other transient signals. Also many different detection devices can be used to detect the transient signals. For example, a thermometer or other heat detection device is used to measure enthalpic changes. Other known detection devices can be used to detect fluorescence, radioactivity and the like. The detection devices need not be located on the surface where the drops are merged. Instead, the detection devices can be spaced a distance from the drop-merging surface. The anti-evaporation devices disclosed herein can limit deleterious effects that may result from evaporation of the sample, and/or allow more time for the detection of transient signals.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications, variations, improvements, and substantial equivalents.

The invention claimed is:
1. A detection system comprising:
a detection device comprising a region including electrodes spaced from one another to merge at least two small, separate drops placed on the electrodes and a thermometer configured and placed within the region to detect a potential signal generated by merger of the drops, a thermometer comprising a thermistor material with current being passed through it from an external source; and
an anti-evaporation device, comprising a cap having at least one cavity that is positioned above and in contact with an upper surface of the detection device, forming a seal around the region, and at least substantially enclosing the region to inhibit mass transport from the drops out of the region such that evaporation from the region does not thermally dissipate the signal during a detection period of less than or equal to 4 seconds at 37° C. or less than or equal to 25 seconds at 5° C. and pogo pins inserted through the cap without breaking the seal around the at least one cavity for providing electrical connection to the detection device.

2. The system of claim 1, wherein the detection device is a nanocalorimeter.

3. The system of claim 1, wherein the detection device includes a thermopile.

4. The system of claim 1, wherein the anti-evaporation device includes a cap having a cavity that at least substantially encloses the region and has a plurality of passages through the cap spaced from the cavity, the passages formed and positioned such that the pogo pins can be received therein.

5. The system of claim 1, wherein the anti-evaporation device comprises an elastomeric material.

6. The system of claim 5, wherein the anti-evaporation device comprises a rigid material that is less gas and vapor permeable than the elastomeric material and the elastomeric material is positioned at an end of the rigid material.

7. The system of claim 1, wherein the anti-evaporation device includes a cavity, the system further comprising a wetted member disposed in the cavity adjacent and in communication with the region.

8. The system of claim 1, wherein the anti-evaporation device comprises a frame extending from the detection device and at least substantially enclosing the region to define a well.

9. The system of claim 8, wherein the frame comprises a rigid material and an elastomeric material, the elastomeric material being positioned between the rigid material and the detection device.

10. The system of claim 8, wherein the well defines a liquid containing region, and the system further comprising a wetted member disposed in the liquid containing region.

11. The system of claim 8, wherein the anti-evaporation device comprises at least two cavities, wherein a first cavity of the cavities at least substantially encloses the region and a second cavity of the cavities is isolated from the first cavity, the second cavity being adapted to receive a liquid to create a high humidity region.

12. The system of claim 8, wherein the detection device comprises a plurality of regions configured to merge at least two small drops and to detect a potential signal generated by merger of the drops, and the anti-evaporation device comprises at least two cavities, wherein a first of the at least two cavities is configured to enclose at least one of the plurality of regions and wherein a second of the at least two cavities is configured to enclose a region upon which a liquid source is placed.

13. The system of claim 12, wherein the second cavity is configured in a channel configuration that at least substantially surrounds the first cavity.

14. The system of claim 1, wherein the cap includes an elastomeric material that forms a seal around the region when pressed against a surface of the detection device.

15. The system of claim 14, wherein the detection device includes a frame extending upwardly from an upper surface forming a well at least substantially surrounding the region, and the cap contacts the frame.

16. The system of claim 1, wherein the detection device includes a plurality of regions where small drops are merged and a temperature is measured to detect a merger of the drops and the anti-evaporation device comprises a cap including a plurality of cavities, each cavity substantially surrounding at least one respective region.

17. The system of claim 16, wherein each region includes multiple electrodes and thermometers.

18. The detection system of claim 2, wherein the nanocalorimeter includes a gasket formed on an upper surface around the sensing region, wherein the cap presses against the gasket to provide environmental isolation for the drops.

19. The detection system of claim 18, further comprising a frame extending upwardly from an upper surface of the nanocalorimeter forming a well that at least substantially surrounds the sensing region, and the cap contacts the frame.

\* \* \* \* \*